United States Patent [19]

Lem et al.

[11] Patent Number: 5,709,846
[45] Date of Patent: Jan. 20, 1998

[54] IODINATED DERIVATIVES, THEIR PREPARATION AND THEIR USE AS CONTRAST AGENTS IN X-RAY RADIOLOGY

[75] Inventors: Gaël Le Lem, Saint-Cloud; Dominique Meyer, Saint-Maur, both of France

[73] Assignee: Guerbet S.A., Villepinte, France

[21] Appl. No.: 648,168

[22] PCT Filed: Sep. 20, 1995

[86] PCT No.: PCT/FR95/01213

§ 371 Date: May 21, 1996

§ 102(e) Date: May 21, 1996

[87] PCT Pub. No.: WO96/09281

PCT Pub. Date: Mar. 28, 1996

[30] Foreign Application Priority Data

Sep. 22, 1994 [FR] France ................... 94 11326

[51] Int. Cl.$^6$ .................... A61K 49/04; C07C 233/65
[52] U.S. Cl. .................... 424/9.452; 564/153; 514/616
[58] Field of Search .................... 564/153; 424/9.452; 514/616

[56] References Cited

U.S. PATENT DOCUMENTS

| | | | |
|---|---|---|---|
| 4,065,553 | 12/1977 | Tilly et al. | 424/5 |
| 4,065,554 | 12/1977 | Tilly et al. | 424/5 |

FOREIGN PATENT DOCUMENTS

| | | |
|---|---|---|
| 0 354 836 | 2/1990 | European Pat. Off. . |
| WO 92/18167 | 10/1992 | WIPO . |
| WO 93/10824 | 6/1993 | WIPO . |
| WO 94/21600 | 9/1994 | WIPO . |
| WO 95/01966 | 1/1995 | WIPO . |

*Primary Examiner*—Shailendra Kumar
*Attorney, Agent, or Firm*—Jacobson, Price, Holman & Stern, PLLC

[57] ABSTRACT

Polyiodinated derivatives of formula:

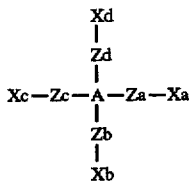

in which

A is a moiety from an aromatic or aliphatic molecule,

Za, Zb, Zc and Zd is Tz-Qz-Vz wherein Tz and Vz are O, COND or NDCO, and D is H or $C_1$ to $C_6$ alkyl or hydroxyalkyl and Qz is $C_1$ to $C_6$ alkylene or hydroxyalkylene or wherein Vz has the above meanings and Qz and/or Tz do not exist, Xa, Xb, Xc and Xd, which are identical or different, have formula

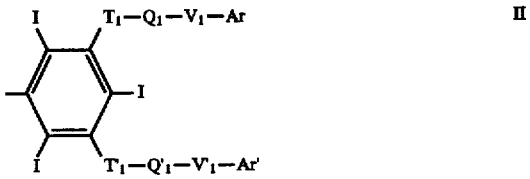

in which Ar and Ar' are tri- or tetraiodinated phenyl groups carrying one or two amide groups substituted by optionally hydroxylated alkyls and T, Q and V have one of the meanings of the Tz, Qz and Vz, or X have, formula

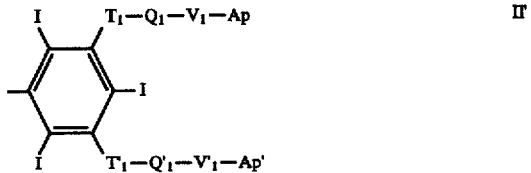

in which Ap and A'p have the above formula II and the T, Q and V groups have one of the meanings of the Tz, Qz and Vz.

Use of these products as contrast agents in X-ray radiology.

22 Claims, No Drawings

IODINATED DERIVATIVES, THEIR PREPARATION AND THEIR USE AS CONTRAST AGENTS IN X-RAY RADIOLOGY

This application is a 371 of PCT/FR95/01213, filed Sep. 20, 1995, published as WO96/09281 Mar. 28, 1996.

The present invention relates to contrast agents for X-ray radiology.

These molecules, with a high molecular weight since they comprise at least 12 triiodinated phenyl rings, have a vascular persistence which is markedly greater than that of the contrast agents currently used in diagnostic, such as iobitridol or iohexol, and more or less analogous to that of compositions resulting from grafting of iodinated rings to polymers, which compositions are known to suffer from disadvantages due to the presence of molecules of various molecular weights in the same sample. Thus, it has been observed that, five minutes after intravenous injection in rat of products of the invention or of commercial contrast agents containing the same dose of iodine, the blood iodine concentration of the new compounds was at least three times higher.

Moreover, the aqueous solutions of these new compounds have a viscosity which is compatible with their intravenous administration in man, at usual doses, whereas their osmolality generally has to be raised.

The compounds of the invention have the formula

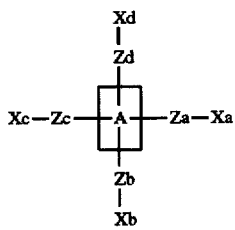

in which $Z_a$, $Z_b$, $Z_c$ and $Z_d$, which are identical or different, are Tz-Qz-Vz, Tz being attached to A;

and Tz and Vz, which are identical or different, are O, COND or NDCO with D representing H or $C_1$ to $C_6$ alkyl, hydroxyalkyl or polyhydroxyalkyl and Qz represents $C_1$ to $C_6$, preferably $C_1$ to $C_4$, alkylene, hydroxyalkylene or polyhydroxyalkylene; or else Qz and/or Tz do not exist;

$X_a$, $X_b$, $X_c$ and $X_d$, which are identical or different, are

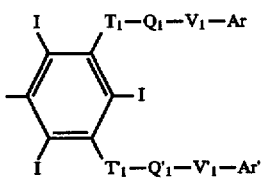

and $T_1$, $T'_1$, $V_1$ and $V'_1$, which are identical or different, are CO—ND' or ND'-CO with D' representing H or $C_1$ to $C_6$ alkyl, optionally carrying one or more OH groups;

$Q_1$ and $Q'_1$, which are identical or different, $C_1$ to $C_6$, and preferably $C_1$ to $C_4$, alkylene optionally carrying one or more OH groups;

Ar and Ar', which are identical or different, have either formula III or formula IV

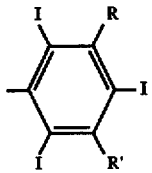

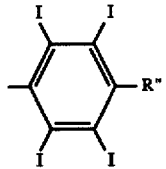

in which formula III, R is COOH and R' is CO—NR'$_1$R'$_2$ or N(R'$_1$)—CO—R'$_2$, R'$_1$ and R'$_2$ being H or $C_1$ to $C_8$ alkyl, hydroxyalkyl or polyhydroxyalkyl, and containing between them more than 4 OH groups; or in which R and R', which are identical or different, are CO—NR'$_1$R'$_2$ or N(R'$_1$)—CO—R'$_2$ and R'$_1$ and R'$_2$ are H or $C_1$ to $C_8$ alkyl, hydroxyalkyl or polyhydroxyalkyl and R and R' contain between them more than 6 OH groups or, better, more than 8 OH groups and preferably 10 OH groups;

and in which formula IV, R" is CO—NR'$_1$R'$_2$ or N(R'$_1$)—CO—R'$_2$, R'$_1$ and R'$_2$ being $C_1$ to $C_8$ hydroxyalkyl or polyhydroxyalkyl such that they contain between them more than 8 OH groups and preferably more than 10 OH groups;

or formula V or formula VI

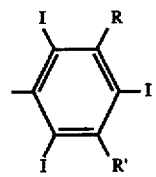

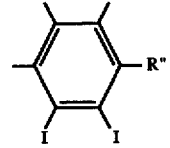

in which formula V, R and R', which are identical or different, respectively are $T_2$-$Q_2$-$V_2$-$Ar_2$ and $T'_2$-$Q'_2$-$V'_2$-$Ar'_2$, with $T_2$, $T'_2$, $Q_2$, $Q'_2$, $V_2$ and $V'_2$ respectively having one of the meanings of $T_1$, $Q_1$ and $V_1$ groups and $Ar_2$ and $Ar'_2$ having the meanings of formulae III or IV;

and in which formula VI, R" is $T_2$-$Q_2$-$V_2$-$Ar_2$, which can have one of the meanings given for formula V;

and A is a biocompatible moiety from an aliphatic or aromatic molecule, optionally containing one or more heteroatoms selected in particular from oxygen, nitrogen and halogens and particularly iodine, said moiety with a molecular weight of less than 2000, having a structure such that the four $Z_a$, $Z_b$, $Z_c$ and $Z_d$ groups can be linked thereto giving amide or ether groups.

Aliphatic moiety is understood to mean a cyclic or acyclic moiety in which the free bonds are situated on several atoms.

Mention may be made, among the A(Tz) moiety according to the invention, of:

tetrakis derivatives of methane, such as:

C(CH$_2$CONH)—$_4$, prepared from the tetraacid compound described in J. Chem. Soc., 1638 (1922)

C(CH₂O(CH₂)₂CONH)—₄, the corresponding acid of which is described in U.S. Pat. No. 2,401,607

C(CH₂O)—₄, derived from tetrakis (hydroxymethyl) methane

C(CH₂NHCO)—₄, prepared from the tetraamine described in J. Chem. Soc., 1588–1595 (1938)

or the tetracarboxamido moieties which are derivatives of 1,2,3,4-butanetetracarboxylic acid, of triethylenetetramine, of ethylenediaminetetraacetic acid and of 1,4,7,10-tetraazacyclododecane-N,N'N",N'"-tetraacetic acid.

An aromatic moiety comprises one or several phenyl rings and optionally $C_1$ to $C_4$ alkyl groups which can be bonded to the phenyl ring directly or via a functional group such as an ether or an amide group, it being possible for the free bonds of said moiety to be or not on the rings.

Mention may be made, among the A(Tz) moieties which derive therefrom, of:

tetraamido derivatives of tetrakis (carboxyphenyl) methane described in Angew. Chem. Int. Ed., 25, 1097 (1986), of benzene-1,2,4,5-tetracarboxylic acid described in J. Amer. Chem. Soc., 80, 2322 (1958) and of its iodinated derivatives, as well as the hexaiodinated derivative described in EP-A-0,501,875, of tetrakis (aminophenyl)methane described in Chem. Ber., 109, 2389 (1976) or of tetrakis (aminomethylphenyl) methane described in Angew, Chem. Int. Ed., 25, 1097 (1986).

A can also contain heteroatoms as in aromatic amides, for example oxalic, malonic and succinic acid derivatives of formula

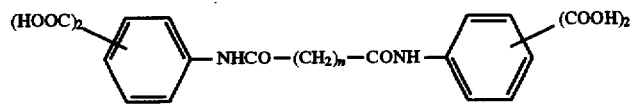

described in Molecular and Biochemical Parasitology, 59, 201–210 (1993), which can be prepared by reaction of aliphatic acid dichlorides with aminobenzenedicarboxylic acids; in the case of their homologous compounds which are iodinated on the phenyl rings, it is preferable to prepare the acid tetrachlorides directly by reaction of oxalic, malonic or succinic acid chlorides, for example, with the dichloride of 5-amino-2,4,6-triiodoisophtalic acid.

The pharmaceutically acceptable salts of the acids of formula I also constitute a subject-matter of the invention.

Alkyl groups can be linear or branched.

$R'_1$ and $R'_2$ groups, on which the hydrophilicity of the molecule depends, will advantageously be hydroxylated and better still will contain at least 6 hydroxyl groups between them.

Preference is given to compounds in which the T and V substituents are amide groups and better still aromatic secondary amide groups; preference is given among the latter, due to their compactness, to compounds in which the Q substituents are $C_1$ or $C_2$ alkylenes.

Preference is given, among aliphatic A groups, to tetrakis derivatives of methane whereas, aromatic groups, preference is given to derivatives of tetrakiscarboxyphenylmethane, which may or may not be iodinated.

Molecules in which the four substituents of A are identical and better still the two substituents of the triodinated phenyl ring bonded to Z are also identical are more readily accessible.

Compounds in which Ar and Ar' have formulae V and VI stay in the vascular compartment longer than homologous compounds in which Ar and Ar' have formulae III and IV and one type or the other will be chosen depending on the diagnostic information required. The compounds of formula

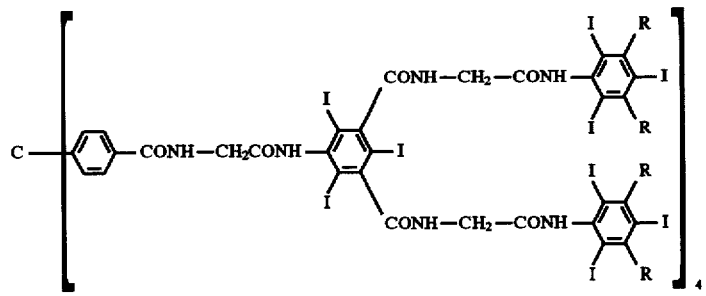

in which R represents $CONR'_1R'_2$, or in which R represents

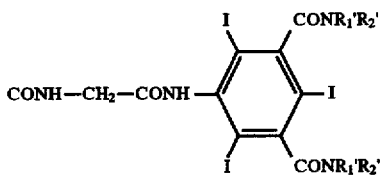

$R'_1$ and $R'_2$ being $C_1$ to $C_8$ hydroxyalkyl or polyhydroxyalkyl and containing between them at least 6 OH groups, are compounds which are particularly useful as blood pool contrast agents for the observation of vascular compartment, due to their molecular structural properties (volume, density, distribution of the hydrophobic and hydrophilic regions) and to their biocompatibility (solubility, toxicity), for iodine doses suitable for examinations.

The process for the preparation of the compounds of formula I is another subject-matter of the invention. These compounds can be prepared by reacting, in the first stage, a A moiety carrying the appropriate functional groups with a triiodinated phenyl derivative of formula

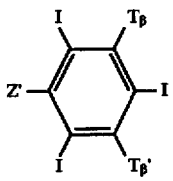

in which $T_\beta$, $T'_\beta$ and Z' are reactive functional groups which are precursors of T, T' and Z groups of formula I, in order to link, to the product obtained, by subsequent stages, $T_1$-$Q_1$-$V_1$-Ar and $T'_1$-$Q'_1$-$V'_1$-Ar' substituents, simultaneously when they are identical or by successive stages.

Nevertheless, it is preferable to prepare first compounds VII carrying a precursor group for Z, of formula

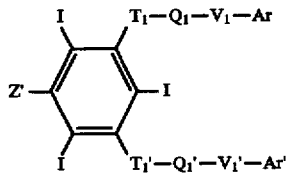

in which T, Q, V and Ar groups have the same meaning as in formula I and Z' which is a reactive precursor group for Z can be COOH, COCl, NDH or OH or Z' is T'z-Qz-Vz, T'z being a precursor group for Tz, and then to react compounds of formula VII with A carrying 4 reactive groups which can be, depending on the nature of Tz to be obtained and of Z': COOH, COCl, NDH, Cl, Br or sulphonate or with A-Tz-Qz-V'z, V'z being a precursor group for Vz; hydroxyl groups can optionally be protected during these reactions.

In both cases, the preparation consists in usual methods for formation of amide groups, from carboxylic acids and amines, or ether groups, from phenols and halides or sulphonates, taking into account the low reactivity of carboxylic acid and acid chloride, amine and hydroxyl groups substituted on a phenyl ring when the two adjacent carbon atoms carry an iodine atom.

More particularly, the process according to the invention comprises:

1) reaction of compound of formula

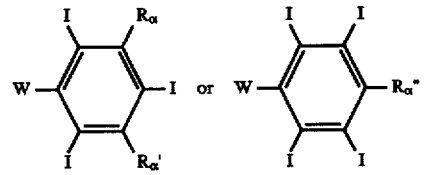

selected according to the nature of Ar and Ar' in the compound of formula I to be obtained, in which $R_\alpha$, $R'_\alpha$ and $R''_\alpha$ are, as the case may be, COCl or $NH_2$ and W is a precursor group for V groups selected from, as the case may be, ND'H, COCl and OH, with when $R_\alpha$ groups are COCl, an aminoalcohol of formula $HNR'_1R'_2$, for example in an aprotic solvent and preferably in the presence of a base capable of fixing the hydrochloric acid released or, when $R_\alpha$ groups are $NH_2$, under usual conditions, with $R'_2COCl$ or with $R'_2COOH$ together with a coupling agent such as those used in chemistry of peptides, hydroxyl groups of $R'_2$ optionally being protected during the amidation reaction, this reaction having to be followed, if necessary, by alkylation of the secondary amide obtained, for example with $R'_1Cl$;

2) then reaction of the product obtained with product of formula $T_\alpha$-Q-$V_\alpha$ in which $T_\alpha$ and $V_\alpha$ are precursor groups for T, T' and V, V' groups and Q is, as the case may be, $Q_1$, $Q_2$, $Q'_1$ or $Q'_2$, $T_\alpha$ optionally being protected as well as the OH groups of the Q groups, in order to form $T_\alpha$-Q-V-Ar product either during an amidation reaction when one of W and $V_\alpha$ is COCl end the other is ND'H or, when W is OH and $V_\alpha$ is Cl, Br or a sulphonate, during an usual etherification reaction, in the presence of a strong base in a polar solvent;

3) and, when Ar and Ar' in formula I have formula V or formula VI, reaction of one or two $T_\alpha$-Q-V-Ar products obtained in the preceding stage with, as the case may be,

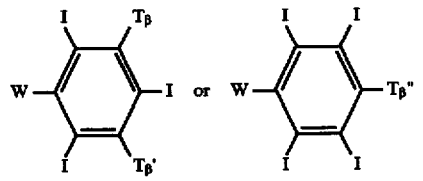

and then that of the product obtained with a $T_\alpha$-Q-$V_\alpha$ defined as in Stage 2 with the product of formula

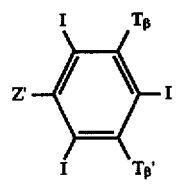

in which $T_\beta$ and $T'_\beta$, which are identical or different, are precursor groups for $T_1$ and $T'_1$, that is to say are groups which, by reaction with W and W', will form $T_1$ and $T'_1$, and Z' is a group which can, with suitable groups situated on A, form Za, Zb, Zc and Zd 4) or, when Ar and Ar' in the formula I are formula III or formula IV, the reaction of one or two $T_\alpha$-$V_\alpha$-Ar products with compound XI 5) and finally reaction of one or several of these groups with A(Z"a)(Z"b)(Z"c)(Z"d), Z" groups, which can be identical or different, being reactive groups selected in order to form an amide or ether bond with Z' groups, these reactions being, depending on the nature of the compound of formula I, etherification or amidation reactions. The order of the stages can be reversed, in particular Stages 1 and 2.

W can also represent $T_\alpha$-Q-V, in which case Stage 2 and, as the case may be , part of Stage 3 are not performed, it being understood that compounds VIII and IX have been prepared beforehand by reaction of $T_\alpha$-Q-$V_\alpha$ with tri- or tetraiodinated phenyl derivative carrying appropriate COOH, OH or ND'H groups.

When Z' is W, before the final coupling with A, it may be modified in order to obtain a precursor for Z.

When R is COOH, it may be protected as an ester, for example methyl ester , which ester can be hydrolysed in the last stage before possibly making a salt.

Triiodinated or tetraiodinated phenyls carrying the appropriate carboxylic acid, amine or phenolic functional groups are known or may be prepared by usual reactions. For example, 5-aminotriiodoisophthalic acid and 3,5-diaminotriiodobenzoic acid described in GB 782,313 result from iodination by ICl of the corresponding amino acids; triiodotrimesic acid may be prepared by diazotization, cyanation and hydrolysis of 5-aminotriiodoisophthalic acid whereas 5-hydroxytriiodoisophthalic acid described in Chem. Abs., 69 86643–6 may be obtained by iodination of the commercial acid.

The acid chlorides of these compounds may be prepared as usual, by reaction with thionyl chloride, optionally in a neutral solvent such as a chlorinated or aromatic hydrocarbon.

The aminoalcohols necessary for the preparation of the $CONR'_1R'_2$ groups are known or may be prepared by analogous processes. Mention may be made, among those preferred in which $R'_1$ and $R'_2$ each contain at least one hydroxyl group, of those in which $$-R'_1 = CH_2(CHOH)_4-CH_2OH$$

$R'_2 = CH_2-(CHOH)_4-CH_2OH$ or $CH_2-CHOH-CH_2OH$ or $CH_2-CH_2OH$, which are commercially available

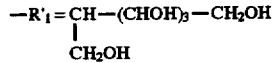

$R'_2 = CH_2-CHOH-CH_2OH$, described in EP-A-558,395

$R'_1=R'_2=CH_2-(CHOH)_3-CH_2OH$, described in J. Org. Chem., 35(2), 464–7 (1970)

$R'_1=R'_2=CH_2-(CHOH)_2-CH_2OH$, described in U.S. Pat. No. 4,661,646.

Other aminoalcohols may be prepared by disubstitution of benzylamine with a halogenated or sulphonated derivative of the appropriate alcohol, followed by debenzylation of the compound obtained, in particular by reaction with $H_2$. It is also possible to react a hydroxylated aldehyde, such as a saccharide, with a primary aminoalcohol and to reduce the imine obtained by reaction with $H_2$ in order to obtain, for example, the compounds with

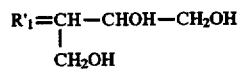

$R'_2 = CH_2-CHOH-CH_2OH$ or $CH_2-(CHOH)_2-CH_2OH$ or $R'_1=CH_2-(CH)H)_3-CH_2OH$ $R'_2=CH_2-CHOH-CH_2OH$ or $CH_2-(CHOH)_2-CH_2)$.

In the case where the iodinated phenyl ring caries two acid chloride or amine groups, asymmetric compounds can be prepared by successively reacting the two chains to be coupled to the ring with, during the first coupling, an amount of chain limited to one stoichiometric equivalent.

Mention may be made, among dehydrating reactants which can be used for the preparation of the amides by direct reaction of an acid with the appropriate amine, of 1-ethoxycarbonyl-2-ethoxy-1,2-dihydroquinoline, 1-(3-dimethylaminopropyl)-3-ethylcarbodiimide or N,N'-dicyclohexylcarbodiimide, optionally together with hydroxybenzotriazole or other agents known in the chemistry of peptides.

The invention also relates to contrast agents for X-ray radiology which comprise, as radiation-absorbing compound, at least one of the compounds according to the invention.

These products in a suitable pharmaceutical form can be administered orally, rectally or parenterally, including intravenous, intra-arterial, intrabronchial or intra-arachnoidal route; the excipients can be selected from those usual in the field and can be used in combination with additives known for adjusting the pH or the osmolality and for decreasing some of the known side effects of the iodinated derivatives.

For parenteral administration, in particular intravascular administration, preference is given to aqueous solutions having pH about 7 which contain from 5 to 40 g of iodine linked to aromatic rings per 100 ml. Depending on the type of diagnostic examination carried out, from 5 ml to 250 ml of solution may be administered to the patient.

In the following, a description is given of examples of compounds which are within the invention and, beforehand, of the preparation of compounds of formula VIII to XI.

A—Preparation of the compound $C_1$ of formula VIII with
$W=T_\alpha-Q-V=H_2N-CH_2-CO-NH$
$R_\alpha=R'_\alpha=CO-N(CH_2-CHOH)_4-CH_2OH)_2$

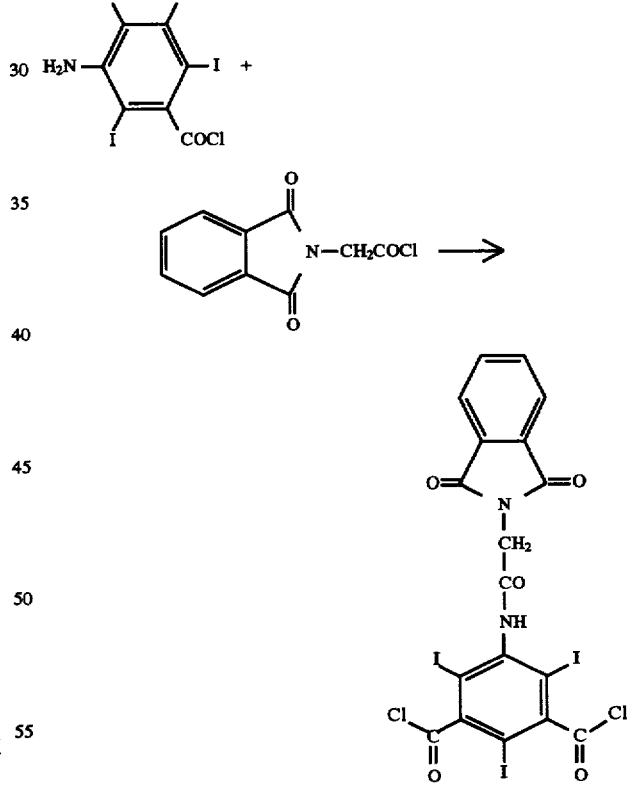

By using the operating conditions described in U.S. Pat. No. 4,283,381, this compound is obtained with a yield of 85%.

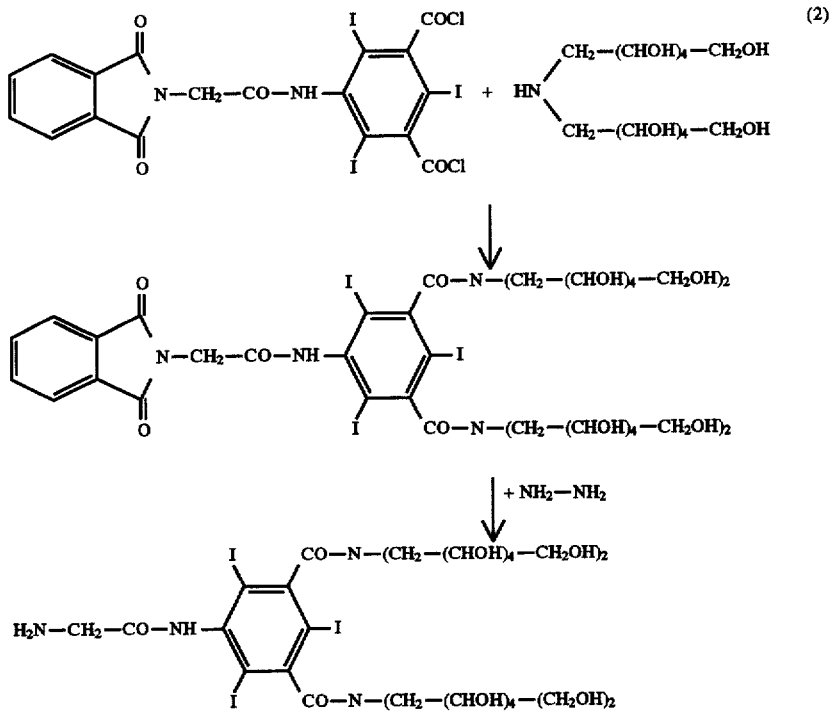

208 g of the above acid dichloride, 416 g of the commercial amine and 100 ml of triethylamine are dissolved in 2 liters of N-methylpyrrolidone or dimethylacetamide and the solution is maintained at 70° C. for 24 hours. The precipitate formed is separated off and the solvent is removed by distillation under reduced pressure. The residue, dissolved in the minimum amount of water at pH 3, is passed through a cationic ion exchange resin (1.5 l of Amberlite® IRN77 marketed by Rohm and Haas in the acid form) in order to remove impurities.

33.2 ml of hydrazine hydrate are added to a solution of the diamide thus obtained in 1.4 liters of water and the mixture is maintained at 80° C. for 3 hours. Acidification is carried out at room temperature by addition of 53 ml of a 10N aqueous hydrochloric acid solution and the precipitate formed is separated off.

The residual solution is passed through an ion exchange resin column containing approximately 1 liter of basic Amberlite® IRA67, then through a column containing 150 ml of Amberlite® IRC50 in the acid form and then grafted onto 4 liters of Amberlite® 200C, from where the expected product is eluted with an aqueous $NH_4OH$ solution.

The eluate is concentrated under reduced pressure. Yield 70%.

HPLC chromatography: LiCrosphere C 18;5 µm column (Merck)—h=25 cm; d=4 mm.

Eluent*: 5/95 $CH_3CN$/0.05M P.I.C.® B8 (Waters); flow rate of 1 ml/minute

Retention time of isomers: approximately 8 minutes

*: P.I.C. B8: Octanesulphonic acid/methanol/calcium acetate/water mixture.

B—Preparation of the compound $C_2$ of formula VII with

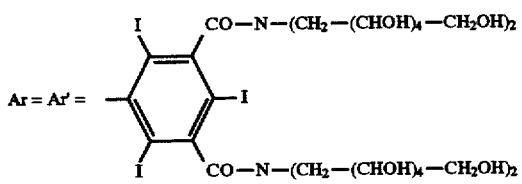

$T_1-Q_1-V_1=T'_1-Q'_1-V'_1=CO—NH—CH_2—CONH$
$Z'=H_2H—CH_2—CONH$

A solution of 59 g of the acid dichloride described in A-1, 200 g of the primary amine VIII obtained in A and 29.5 ml of tributylamine in 400 ml of N-methylpyrrolidone or dimethylacetamide is maintained at 70° C. for 24 hours. The solvent is removed under reduced pressure and the residue is chromatographed on 3 kg of silanized silica RP2, marketed by Merck (GER), elution being carried out with water, or on 4 kg of adsorbant XAD (marketed by Rohm and Baas), elution being carried out with a $CH_3OH/H_2O$ mixture.

The product, obtained with a yield of 50%, is treated with hydrazine hydrate, as described above, to give the expected compound (Yield 45%).

The elution volume of this compound during filtration through a Superdex® 30 gel in a 16 mm×60 cm column, marketed by Pharmacia, in a buffer at pH=7.2 comprising 0.1M NaCl, 0.05M $NaH_2PO_4$ and 0.01M $NaN_3$, with a flow rate of 1 ml/minute, is 102 ml for an injected sample of 1 mg in 250 µl of buffer.

HPLC chromatography: Symmetry® C 18;5 µm column (Waters)—h=25 cm; d=4.6 mm.

Eluent: $CH_3CN$/0.01M aqueous $KH_2PO_4$ (15/85) (without $CH_3CN$ for 5 minutes); flow rate 1 ml/minute Retention time of isomers: approximately 18 minutes C—Preparation of compound $C_3$ of formula VII with
$T_1-Q_1-V_1=T'_1-Q'_1-V'_1=CO—NH—CH_2—CONH$

Z'=H₂N—CH₂—CONH

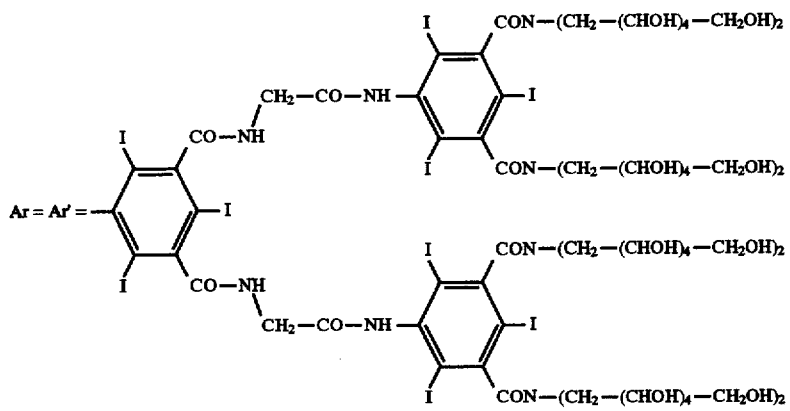

5.65 g of the acid dichloride of Stage A-1, 48 g of the primary amine VII obtained according to Band 3 ml of tributylamine in 100 ml of N-methylpyrrolidone are maintained at 70° C. for 24 hours. After purification as according to B, the derivative containing the 7 iodinated phenyl rings is treated with hydrazine hydrate to give the crude primary amine. The latter is purified by passing through ion exchange resins in the acid and basic form as in the preparation B, optionally followed by ultrafiltration with a Minisette filter unit of nova type marketed by Filtron (USA) with a membrane with a cutoff threshold of 10 kdaltons, during which the desired product passes into the filtrate. Yield: 65%.

The elution volume of this product under the same operating conditions as in the preparation B is 91 ml, whereas it is 111 ml on a Superdex® 75 column.

HPLC chromatography: Symmetry® C 18;5 µm column (Waters)—h=25 cm; d=4.6 mm.

Eluent: CH₃CN/0.01M aqueous KH₂PO₄ (15/85) (without CH₃CN for 5 minutes); flow rate 1 ml/minute.

Retention time of the isomers: approximately 23 minutes

D—Preparation of compound $C_4$ of formula VIII with
W=T$_\alpha$-Q-V=H₂N—CH₂—CONH
R$_\alpha$=COOH

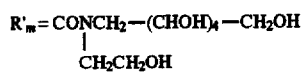

1) 239 g of acid dichloride described in the preparation A-1, 83 g of

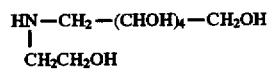

marketed by Aldrich and 39 ml of triethylamine are dissolved in 1 l of N,N-dimethylacetamide. After 24 hours at room temperature, 300 ml of water are introduced into the mixture which is then maintained for 48 hours at 45° C. in order to hydrolyse the remaining acid chloride. The solvents are then removed by distillation under reduced pressure and the residue is purified as above by passing through a column containing 500 ml of Amberlite® IRN77 and one containing 3 kg of silanized silica RP2 marketed by Merck.

The monoamide is thus obtained with a yield of 40%.

2) This compound is treated with hydrazine hydrate and purified by passing through acid and basic ion exchange resins as in the preparation A. Yield 70%.

E—Preparation of compound $C_5$ of formula VII with
T₁-Q₁-V₁=T'₁-Q'₁-V'₁=CO—NH—CH₂—CONH
Z'=H₂N—CH₂—CONH

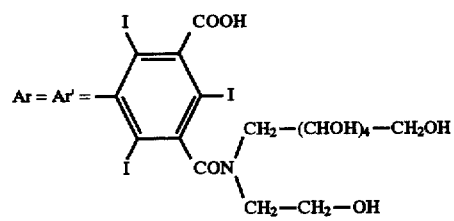

With operating conditions similar to those described for the preparation B, the desired compound is obtained with a yield of 30%.

Its elution volume under the conditions indicated above on Superdex® 30 is 92 ml.

EXAMPLE 1

Compound No. 1 of formula I in which

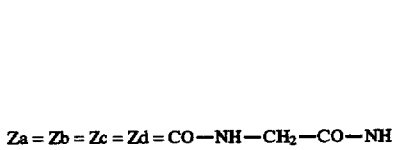

-continued

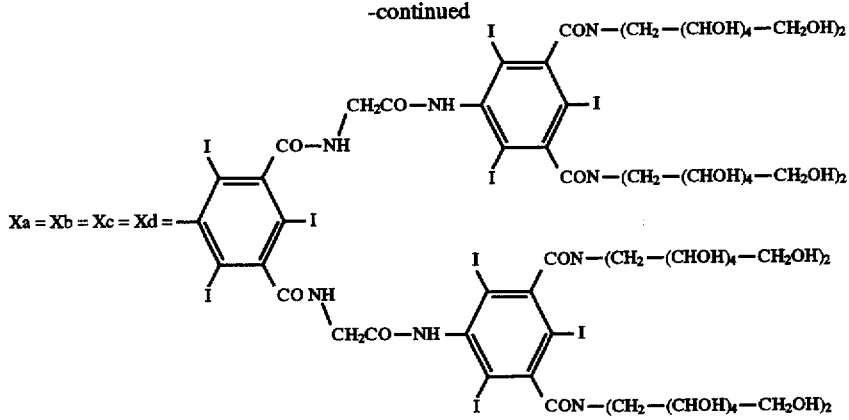

A solution of 15.3 g of the compound obtained according to the preparation B, 0.486 g of tetrakis(carboxyphenyl) methane, 0.768 g of 1-hydroxybenzotriazole, 1.09 g of 1-(3-dimethylaminopropyl)-3-ethylcarbodiimide and 1 ml of triethylamine in 100 ml of dimethylformamide is brought to 40° C. and this temperature is maintained for 6 hours before removal of the solvent by distillation under reduced pressure.

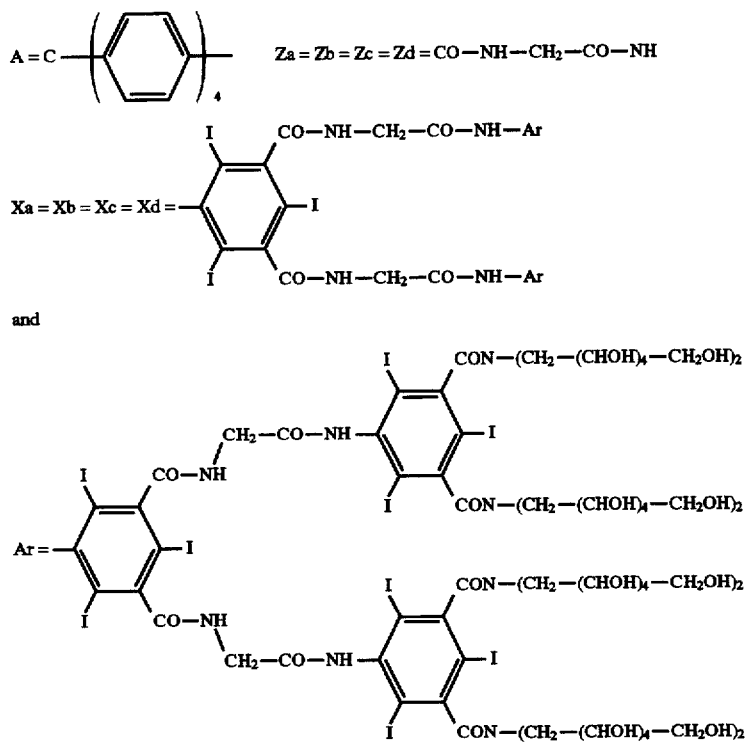

and

The residue is dissolved in the minimum amount of water and subjected to diaultrafiltration with a Minisette® filter unit of nova type marketed by Filtron (USA) with a membrane made of polyethersulphone with a cutoff threshold of 5 kdaltons. Yield 95%.

The elution volume for this compound, determined under the same gel filtration conditions as above, is 49 ml (Superdex® 30).

EXAMPLE 2

Compound No. 2 of formula I in which

The compound prepared in C is reacted with tetrakis (carboxyphenyl)methane under operating conditions similar to those described in the preceding example, with the exception of the ultrafiltration, which takes place through a membrane with a cutoff threshold of 10 kdaltons.

The compound of formula I, obtained with a yield of 90%, has an elution volume of 85 ml in gel filtration under the conditions described above (Superdex® 75).

EXAMPLE 3

Compound No. 3 of formula I in which

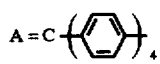

Za = Zb = Zc = Zd = CO—NH—$CH_2$—CO—NH

Xa = Xb = Xc = Xd =

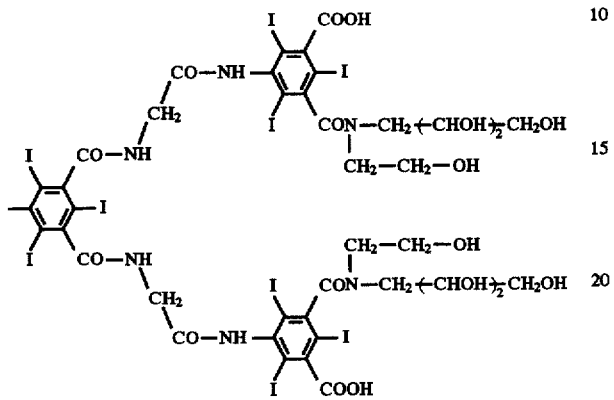

20 g of compound VII obtained in the preparation E, 0.89 g of tetrakis(carboxyphenyl)methane, 1.41 g of 1-hydroxybenzotriazole, 2 g of 1-(3-dimethylaminopropyl)-3-ethylcarbodiimide and 1.5 ml of triethylamine are dissolved in 200 ml of dimethylformamide and the reaction mixture is maintained at 40° C. for 6 hours. After removal of the solvent, the residue is dissolved in water and then subjected to ultrafiltration as above but with a membrane with a cutoff threshold of 3 kdaltons.

The final product precipitates by addition of concentrated HCl to the mixture.

Yield 87%.

Its elution volume, determined under the above gel filtration conditions, is 49 ml (Superdex® 30).

EXAMPLE 4

Preparation of Compounds Nos. 1 and 2 in dimethylacetamide.

0.012 mol of compound $C_2$ or compound $C_3$ are slowly dissolved in dimethylacetamide in the proportion of 25 g/100 ml at a temperature of between 20 and 60° C. approximately. 0.0025 mol of tetrakis(carboxyphenyl)methane, 0.014 mol of N,N'-dicyclohexylcarbodiimide, 0.014 mol of 1-hydroxybenzotriazole and 0.015 mol of triethylamine are then introduced at room temperature. After stirring for 24 hours, 5 volumes of water are added and the solution is ultrafiltered as above to give the expected product in the form of & white powder with a yield of 55%.

These compounds can be characterized by steric exclusion chromatography (SEC) on 4 columns mounted in series marketed by Shodex (JP) under the references OHpaK SB-8.. HQ with a diameter of 8 mm and a length of 30 cm containing a polyhydroxymethacrylate gel: SB-804 (exclusion limit=$10^6$ daltons, pullulan standard)+SB-803 ($10^5$)+SB-802-5 ($10^4$)+SB-802-5. The eluent is a mixture of 0.16M aqueous NaCl solution and acetonitrile (70/30 v/v); flow rate 0.8 ml/minute; temperature 30° C.

The retention time $t_R$ of Compound No. 1 is 34.3 minutes whereas that of the starting compound $C_2$ is 38.7 minutes.

For Compound No. 2, $t_R$=31.8 minutes and for $C_3$, $t_R$=36.5 minutes.

We claim:
1. A compound of formula

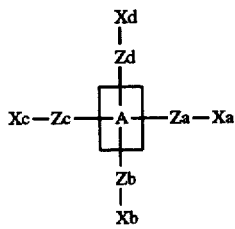

in which

Za, Zb, Zc and Zd, which are identical or different, are Tz-Qz-Vz and Tz and Vz, which are identical or different, are selected from the group consisting of O, CO—ND and ND—CO groups with D being selected from the group consisting of H, $C_1$ to $C_6$ alkyl, hydroxyalkyl and polyhydroxyalkyl and Qz being selected from the group consisting of $C_1$ to $C_6$ alkylene, hydroxyalkylene and polyhydroxyalkylene or QZ and/or Tz do not exist, Xa, Xb, Xc and Xd, which are identical or different, have the following formula II

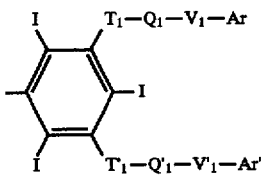

and $T_1$, $T'_1$, $V_1$ and $V'_1$, which are identical or different, are selected from the group consisting of CO—ND' and ND'—CO with D' being selected from the group consisting of H, $C_1$ to $C_6$ alkyl and $C_1$ to $C_6$ alkyl carrying one or several OH groups;

$Q_1$ and $Q'_1$, which are identical or different, are selected form the group consisting of $C_1$ to $C_6$ alkylene and $C_1$ to $C_6$ alkylene carrying one or more OH groups;

Ar and Ar', which are identical or different, are selected from the group consisting of formula III and formula IV:

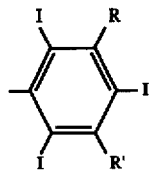

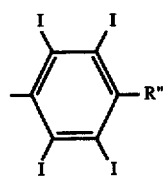

in which formula III, R is COOH and R' is selected from the group consisting of CO—NR'$_1$R'$_2$ and N(R'$_1$)—CO—R'$_2$, R'$_1$ and R'$_2$ being selected from the group consisting of H, $C_1$ to $C_8$ alkyl, hydroxyalkyl and polyhydroxyalkyl, so that they contain between them more than 4 OH groups; or in which R and R', which are identical or different, are selected from the group consisting of CO—NR'$_1$R'$_2$ and N(R'$_1$)—

CO—R'$_2$ and R'$_1$ and R'$_2$ are selected from the group consisting of H, C$_1$ to C$_8$ alkyl, hydroxyalkyl and polyhydroxyalkyl and R and R' contain between them more than 6 OH groups, and in which formula IV, R" is selected from the group consisting of CO—NR'$_1$R'$_2$ and N(R'$_1$)—CO—R'$_2$, R'$_1$ and R'$_2$ being selected from the group consisting of C$_1$ to C$_8$ hydroxyalkyl and polyhydroxyalkyl, such that they contain between them more than 8 OH groups, or Ar and Ar', which are identical or different are selected from the group consisting of formula V and formula VI

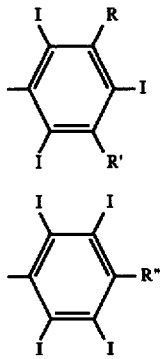

in which R and R', which are identical or different, are selected from the group consisting of T$_2$-Q$_2$-V$_2$-Ar$_2$ and T$_2$-Q'$_2$-V'$_2$-Ar'$_2$, T$_2$, T'$_2$, Q$_2$, Q'$_2$, V$_2$ and V'$_2$ groups respectively having the meanings of T$_1$, Q$_1$ are V$_1$ groups and Ar$_2$ and Ar'$_2$ having the meanings of formulae III or IV, and in which formula VI, R" is T$_2$-Q$_2$-V$_2$-Ar$_2$ which can have one of the meanings given for formula V and A is a biocompatible moiety from an aliphatic, alicyclic or aromatic moieties with a molecular weight of less than 2000, the 4 free bonds of which can form a molecule containing an amide or ether group with Za, Zb, Zc or Zd, or its salt with a pharmaceutically acceptable base.

2. A compound according to claim 1, wherein the 4 substituents of A are identical.

3. A compound according to claim 1, wherein R'$_1$ and R'$_2$ are hydroxylated and comprise between them more than 8 OH groups.

4. A compound according to claim 1, wherein R'$_1$ and R'$_2$ are hydroxylated and comprise between them 10 OH groups.

5. A compound according to claim 1, wherein T and V groups are selected from the group consisting of CO—NH and NH—CO groups.

6. A compound according to claim 1, wherein T and V groups are selected from the group consisting of CO—NH and NH—CO groups and Q groups are C$_1$-C$_2$ alkylenes.

7. A compound according to claim 1, wherein A is an aromatic moiety derived from tetrakisphenylmethane.

8. A compound according to claim 1, wherein A is a tetrakis (carboxyphenyl) methane moiety.

9. A compound according to claim 1, wherein A-(Tz)$_4$ have formula

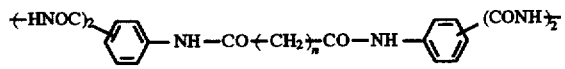

in which n is selected from the group consisting of 0, 1 and 2 and in which the phenyls are optionally iodinated.

10. A compound of formula I according to claim 1, wherein Ar and Ar' have formula III

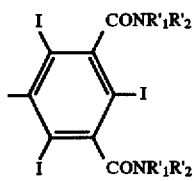

11. A compound of formula I according to claim 1, wherein Ar and Ar' are

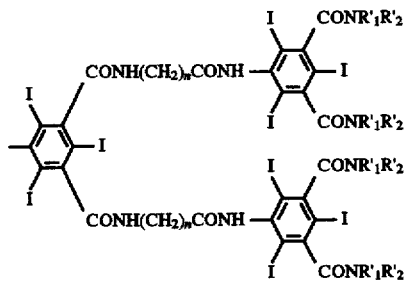

n being selected from the group consisting of 1 and 2.

12. A contrast agent composition for X-ray radiology which comprises an effective amount of a compound according to claim 1 and a pharmaceutically acceptable excipient.

13. A compound according to claim 1 wherein the 4 substituents of A are identical and R'$_1$ and R'$_2$ are hydroxylated and comprise between them more 8 OH groups.

14. A compound according to claim 1 wherein the 4 substituents of A are identical and R'$_1$ and R'$_2$ are hydroxylated and comprise between them more than 10 OH groups.

15. A compound according to claim 1 wherein the 4 substituents of A are identical, T and V groups are selected from the group consisting of CONH and NHCO groups, Ar and Ar' which are identical are selected from the group consisting of groups of formula III and V and R'$_1$ and R'$_2$ are hydroxylated and comprise between them more than 8 OH groups.

16. A compound according to claim 1 wherein the 4 substituents of A are identical, T and V groups are selected from the group consisting of CONH and NHCO groups, Ar and Ar' which are identical are selected from the group consisting of groups of formula III and V and R'$_1$ and R'$_2$ are hydroxylated and comprise between them more than 10 OH groups.

17. A compound according to claim 1 wherein A is a tetrakis (carboxyphenyl) methane moiety, T and V groups are selected from the group consisting of CONH and NHCO groups, Ar and Ar' which are identical are selected from the group consisting of groups of formula III and V and R'$_1$ and R'$_2$ are hydroxylated and comprise between them more than 8 OH groups.

18. A compound according to claim 1 wherein A is a tetrakis (carboxyphenyl) methane moiety, T and V groups are selected from the group consisting of CONH and NHCO groups, Ar and Ar' which are identical are selected from the group consisting of groups of formula III and V and R'$_1$ and R'$_2$ are hydroxylated and comprise between them more than 10 OH groups.

19. A compound according to claim 1 wherein A is a tetrakis (carboxyphenyl) methane moiety, T and V groups are selected from the group consisting of CONH and NHCO groups, Ar and Ar' which are identical are selected from the group consisting of groups of formula

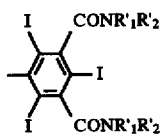

and

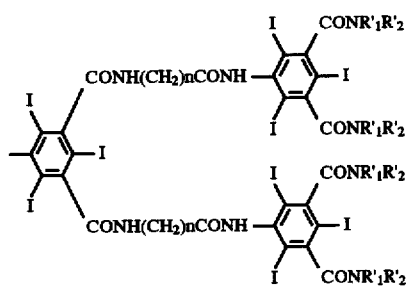

in which n is selected from the group consisting of 1 and 2 and R'₁ and R'₂ are hydroxylated and comprise between them more than 8 OH groups.

20. A compound according to claim 1 wherein A is a tetrakis (carboxyphenyl) methane moiety, T and V groups are selected from the group consisting of CONH and NHCO groups, Ar and Ar' which are identical are selected from the group consisting of groups of formula

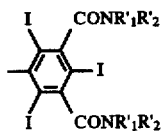

and

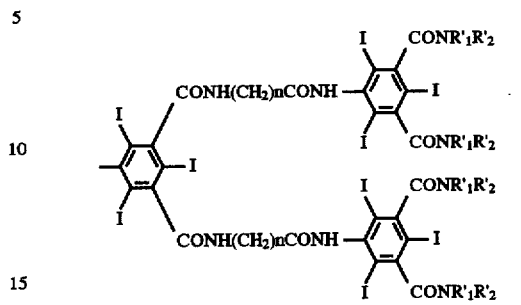

in which n is selected from the group consisting of 1 and 2 and

R'₁ and R'₂ are hydroxylated and comprise between them more than 10 OH groups.

21. A contrast agent composition for X-ray radiology which comprises an effective amount of a compound according to claim 18 and a pharmaceutically acceptable excipient.

22. A contrast agent composition for X-ray radiology which comprises an effective amount of a compound according to claim 20 and a pharmaceutically acceptable excipient.

* * * * *